(12) United States Patent
Evering et al.

(10) Patent No.: US 8,104,352 B2
(45) Date of Patent: Jan. 31, 2012

(54) PRESSURE MEASUREMENT UNIT FOR DETERMINING FLUID PRESSURE WITHIN MEDICAL DISPOSABLES

(75) Inventors: Hans-Gerd Evering, Corseaux (CH); Didier Vecten, Ballens (CH); Florent Junod, Veigy-Foncenex (FR)

(73) Assignee: Debiotech S.A., Lausanne (CH)

( * ) Notice: Subject to any disclaimer, the term of this patent is extended or adjusted under 35 U.S.C. 154(b) by 496 days.

(21) Appl. No.: 12/161,084

(22) PCT Filed: Jan. 20, 2007

(86) PCT No.: PCT/IB2007/050196
§ 371 (c)(1),
(2), (4) Date: Dec. 15, 2008

(87) PCT Pub. No.: WO2007/085993
PCT Pub. Date: Aug. 2, 2007

(65) Prior Publication Data
US 2009/0277276 A1 Nov. 12, 2009

(30) Foreign Application Priority Data
Jan. 26, 2006 (EP) .................................. 06100885

(51) Int. Cl.
*G01L 7/00* (2006.01)
(52) U.S. Cl. .......................................... 73/706; 73/715
(58) Field of Classification Search .................. None
See application file for complete search history.

(56) References Cited

U.S. PATENT DOCUMENTS

| | | | |
|---|---|---|---|
| 5,551,300 A | 9/1996 | Vurek et al. | |
| 6,117,086 A * | 9/2000 | Shulze | 600/488 |
| 7,021,148 B2 * | 4/2006 | Kuhn et al. | 73/715 |
| 7,168,334 B1 * | 1/2007 | Drott | 73/866.5 |
| 2003/0200812 A1 | 10/2003 | Kuhn et al. | |
| 2004/0050168 A1 | 3/2004 | Uberreiter et al. | |

OTHER PUBLICATIONS

International Search Report for PCT/IB2007/050196, mailed Jun. 1, 2007.
Written Opinion for PCT/IB2007/050196, mailed Jun. 1, 2007.

* cited by examiner

*Primary Examiner* — Lisa Caputo
*Assistant Examiner* — Jermaine Jenkins
(74) *Attorney, Agent, or Firm* — Nixon & Vanderhye P.C.

(57) ABSTRACT

The present invention relates to a pressure measurement unit to determine positive and negative fluid pressure within a disposable for medical devices. As part of the disposable, the invention consists of a rigid measurement chamber, which is covered by an elastic form part. This measurement chamber can be connected to a medical device, which is equipped with a pressure transducer. Specific shapes of the elastic form part and specific instrument interfaces ensure the connection between this elastic form part, the measurement chamber and the pressure transducer to exclude the influence of atmospheric pressure during measurements. The coupling and the sealing ability against atmospheric pressure is controllable. Such pressure measurement units can be used to measure fluid pressure in disposable to control for example fluid pumps.

10 Claims, 2 Drawing Sheets

PRESSURE MEASUREMENT UNIT FOR DETERMINING FLUID PRESSURE WITHIN MEDICAL DISPOSABLES

This application is the U.S. national phase of International Application No. PCT/I132007/050196 filed 20 Jan. 2007 which designated the U.S. and claims priority to European Patent Application No. 06100885.0 filed 26 Jan. 2006, the entire contents of each of which are hereby incorporated by reference.

FIELD OF INVENTION

The present invention relates to pressure measurement in medical devices, for instance in a disposable.

STATE OF THE ART

The interface of a disposable with a medical device requires technical solutions which should be simple and reliable. Specifically for measurement purposes, the design must insure the functionality and controllability. A pressure transducer must be protected against damaging. The mechanical engagement between disposable and instrument should be performed and controlled by the instrument. Any malfunction should be reported to the user.

The current technical solutions are not able to fulfil all necessary requirements. Initially, their design was made for the use in clinical environments and to be handled by medical staff and not for example at patient's home environments.

There is therefore a need to improve the pressure measurement of fluid in medical devices.

GENERAL DESCRIPTION OF THE INVENTION

The above cited problem is solved with the present invention which concerns a fluid pressure measuring unit for medical devices comprising a medical fluid chamber defined by rigid walls and one elastic wall. The medical fluid chamber comprises a medical fluid inlet and a medical fluid outlet. The fluid pressure measuring unit furthermore comprises a pressure transducer having a planar measuring surface, said elastic wall and said planar measuring surface being parallel and separated by a fluid tight chamber.

Advantageously the elastic wall and the transducer are mechanically contacting each others through at least one rigid element and one elastic element.

In a preferred embodiment of the invention, the external face of the elastic wall contains a sealing protrusion on its periphery. The sealing protrusion is adapted to insure a fluid tight sealing between the elastic wall and the rigid element.

Preferably, the elastic wall and the planar measuring surface are horizontal but those elements can also be vertical.

In one embodiment the sealing protrusion has an annular shape and is extending vertically.

In another embodiment the sealing protrusion has also an annular shape but is extending horizontally.

In another embodiment the fluid tight chamber comprises a ventilation channel. A electromagnetic may be advantageously at the outlet of the ventilation channel. Preferably, the fluid tight chamber comprises a circular groove on its lateral wall. The circular groove is designed to act as a ventilation chamber.

DETAILED DESCRIPTION OF THE INVENTION

The invention is discussed below in a more detailed way with examples illustrated by the following figures.

NUMERICAL REFERENCES USED IN THE DRAWINGS

Figure 1:
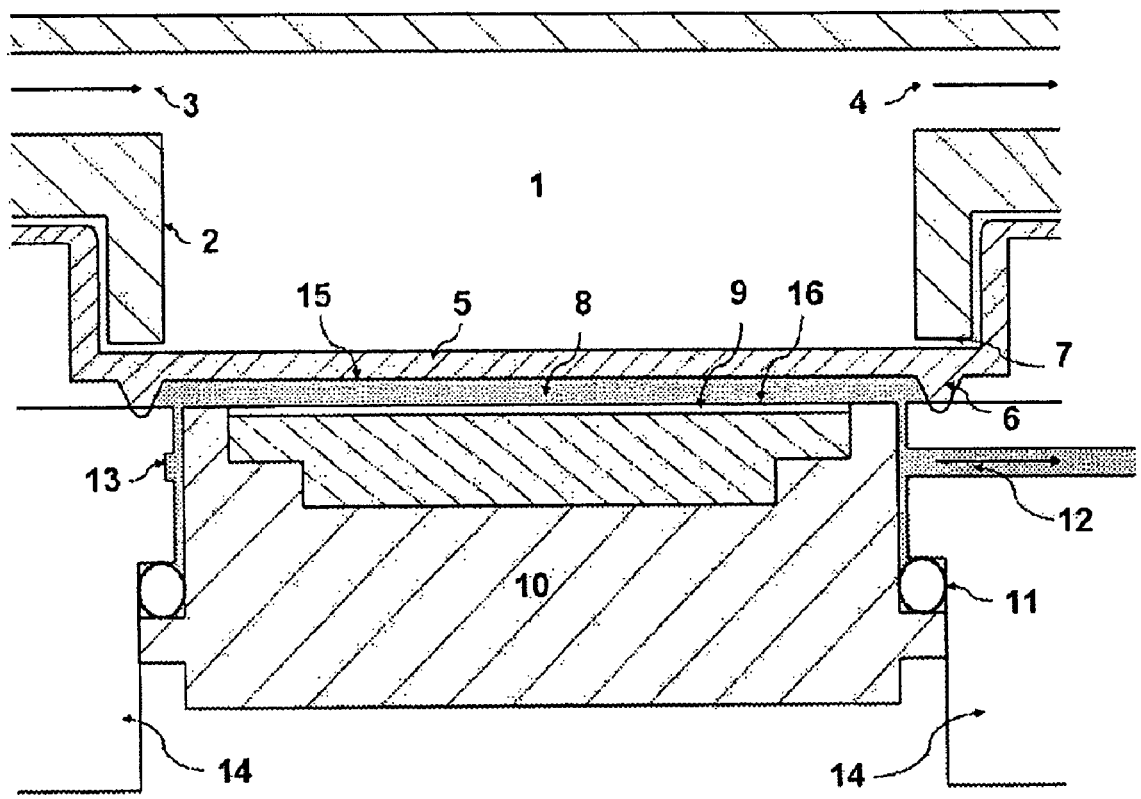
FIG. 1 shows a first embodiment with a vertical sealing between the measuring part and the medical fluid chamber.

1. Medical fluid
2. Rigid chamber
3. Inlet
4. Outlet
5. Elastic wall
6. Sealing rib
7. Sealing rigid wall surface
8. Fluid tight chamber
9. Transducer membrane
10. Transducer
11. O-ring
12. Ventilation channel
13. Ventilation chamber
14. Rigid element
15. Elastic wall external face
16. Measuring surface The description below presents, among others, two solutions to couple a measurement chamber, which is covered with a elastic form part, with a pressure transducer. The two solutions shall be referred herein as vertical and horizontal sealing.

Vertical Sealing (FIG. 1)

The fluid 1, for which pressure has to be measured, is located within a rigid chamber 2 which is forming part of a disposable. The chamber 2 has an inlet 3 and outlet 4. The bottom of the rigid chamber 2 is externally sealed with an elastic wall 5. Additionally, the elastic wall 5 is equipped with a vertical sealing rib 6 of circular shape.

This vertical sealing rib 6 can be pressed by instrument coupling with the circular sealing wall surface 7 of the rigid chamber 2 against the interface plate of the medical device. The sealing wall surface 7 of the rigid chamber 2 creates after insertion a specific force onto the vertical sealing rib 6 to seal the inner system against atmospheric pressure. The interface plate of the medical device is equipped with a pressure transducer 10. The housing of the pressure transducer is hermetic sealed against the atmospheric pressure with the O-ring 11. The instrument coupling ensures, that the membrane 9 of the pressure transducer and the elastic form part 5 will be attached to a small remaining distance, which creates the final air chamber 8.

To ensure, that after the coupling of disposable and instrument the parallel positioning of the elastic form part 5 and the membrane 9 of the pressure transducer 10 will be achieved, a circular space around the transducer housing 13 can be used to ventilate this system with the ventilation channel 12. At the outlet of this ventilation channel a electromagnetic valve is connected (not shown in the drawing).

Figure 2:
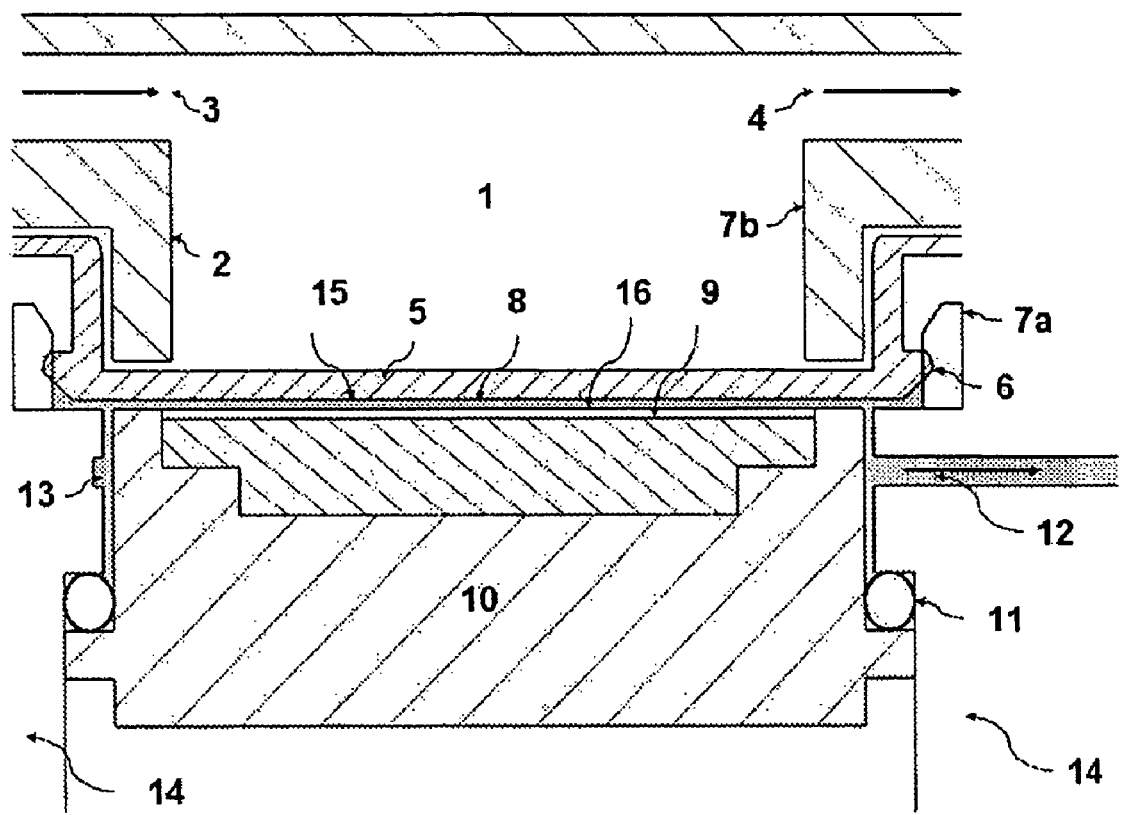
FIG. 2 shows a second embodiment with a horizontal sealing between the measuring part and the medical fluid chamber.

Horizontal Sealing (FIG. 2)

The fluid 1, for which pressure has to be measured, is located within a rigid chamber 2 which is forming part of a disposable. The chamber 2 has an inlet 3 and outlet 4. The bottom of the rigid chamber 2 is externally sealed with an elastic wall 5.

Additionally, the elastic form part 5 is equipped with horizontal sealing geometry 6 in circular shape.

This horizontal sealing geometry 6 will be pressed by instrument coupling in-between the circular sealing wall 7a of the medical device and the partial chamber wall 7b of the rigid chamber 2 and creates after insertion a sealing against atmospheric pressure. The circular sealing wall 7a of the medical device is located above and around a assembled pressure transducer 10. The housing of the pressure transducer is hermetic sealed against the atmospheric pressure with the O-ring 11. The instrument coupling ensures, that the membrane 9 of the pressure transducer and the elastic form part 5 will be moved together to a small remaining distance, which creates the final air chamber 8.

To ensure, that after the coupling of disposable and instrument the parallel positioning of the elastic form part 5 and the membrane 9 of the pressure transducer 10 will be achieved, a circular space around the transducer housing can be used to ventilate this system with the ventilation channel 12. At the outlet of this ventilation channel a electromagnet valve is connected (not shown in the drawing).

How the System Works

In the presence of positive pressure in the liquid 1, the elastic form part 5 will be pushed towards the pressure transducer 10. This mechanical movement will compress the air volume 8 and the increased air pressure will be transmitted to the pressure transducer 10. In the presence of negative pressure in the liquid 1, the elastic form part 5 will be moved in the opposite direction. In this case, the air volume 8 will be decompressed and the decreased air pressure will be transmitted to the pressure transducer 10.

Coupling and Sealing Control

To monitor the correct disposable-instrument coupling and sealing, the ventilation channel shall be closed during the engagement. Therefore a specific overpressure will be created within the air chamber 8 during the coupling and travel process. As soon as the sealing geometry (vertical or horizontal) will trap the air between the elastic form part 5 and the transducer membrane 9, the air pressure within the chamber 8 will increase. This increased pressure signal shall be transmitted and detectable by the pressure transducer. After a specific waiting time, this pressure remains at a constant level, which can be used to confirm the correct sealing against the atmospheric pressure. During opening of the ventilation channel 12, a pressure drop to the atmospheric pressure level is detectable. This procedure can be used to ensure and confirm the correct engagement between disposable and instrument.

The invention claimed is:

1. Fluid pressure measuring unit for medical devices comprising a medical fluid chamber defined by rigid walls and one elastic wall, said medical fluid chamber comprising a medical fluid inlet, a medical fluid outlet, a pressure transducer having a planar measuring surface, and wherein said elastic wall and said planar measuring surface are parallel and separated by a fluid tight chamber, and wherein said fluid tight chamber comprises a ventilation channel.

2. Fluid pressure measuring unit according to claim 1 wherein said elastic wall and said transducer are mechanically contacting each other through at least one rigid element and one elastic element.

3. Fluid pressure measuring unit according to claim 2 wherein the external face of said elastic wall contains a sealing protrusion on its periphery which is adapted to insure a fluid tight sealing between said elastic wall and said rigid element.

4. Fluid pressure measuring unit according to claim 1 wherein said elastic wall and said planar measuring surface are horizontal.

5. Fluid pressure measuring unit according to claim 1 wherein said elastic wall and said planar measuring surface are vertical.

6. Fluid pressure measuring unit according to claim 3 wherein said sealing protrusion has an annular shape and is extending vertically.

7. Fluid pressure measuring unit according to claim 3 wherein said sealing protrusion has an annular shape and is extending horizontally.

8. Fluid pressure measuring unit according to claim 1 wherein said fluid tight chamber comprises a circular groove on its lateral wall, said circular groove being adapted to act as a ventilation chamber.

9. Fluid pressure measuring unit according to claim 1 wherein said fluid tight chamber is designed to contain a gas.

10. Fluid pressure measuring unit according to claim 1 wherein said fluid tight chamber is designed to contain a liquid.

* * * * *